US010772575B2

(12) United States Patent
Suto et al.

(10) Patent No.: US 10,772,575 B2
(45) Date of Patent: Sep. 15, 2020

(54) AUTOMATIC MEASUREMENT POINT CORRECTION METHOD, AUTOMATIC MEASUREMENT POINT CORRECTION APPARATUS AND COMPUTER READABLE MEDIUM STORING AUTOMATIC MEASUREMENT POINT CORRECTION PROGRAM

(71) Applicant: Nihon Kohden Corporation, Shinjuku-ku, Tokyo (JP)

(72) Inventors: Jiro Suto, Tokyo (JP); Tsuneo Takayanagi, Tokyo (JP); Takashi Kaiami, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 331 days.

(21) Appl. No.: 15/217,096

(22) Filed: Jul. 22, 2016

(65) Prior Publication Data
US 2017/0020464 A1 Jan. 26, 2017

(30) Foreign Application Priority Data
Jul. 24, 2015 (JP) .................................. 2015-146782

(51) Int. Cl.
*A61B 5/0452* (2006.01)
*A61B 5/00* (2006.01)
(Continued)

(52) U.S. Cl.
CPC ............ *A61B 5/7475* (2013.01); *A61B 5/044* (2013.01); *A61B 5/04525* (2013.01); *A61B 5/7203* (2013.01); *A61B 5/0456* (2013.01)

(58) Field of Classification Search
CPC ...... A61B 5/0452; A61B 5/0468; G06F 19/00
(Continued)

(56) References Cited

U.S. PATENT DOCUMENTS 5,092,340 A 3/1992 Yamaguchi et al.
5,251,076 A 10/1993 Hagiwara et al.
(Continued)

FOREIGN PATENT DOCUMENTS

CN 103300846 A 9/2013
JP S63-99840 A 5/1988
(Continued)

OTHER PUBLICATIONS

Japanese Office action issued in Japanese Patent Application No. 2015-146782 dated Jun. 25, 2019.

*Primary Examiner* — Jon Eric C Morales
(74) *Attorney, Agent, or Firm* — Pearne & Gordon LLP (57) ABSTRACT

An automatic measurement point correction method includes acquiring vital signs information waveform data indicating a vital signs information waveform having a plurality of waveforms which periodically appear on a time axis, determining a plurality of measurement points for measuring a predetermined measurement item of each waveform included in the vital signs information waveform, causing the vital signs information waveform and measurement point displayers to be displayed on a displaying section, correcting a first measurement point for measuring the predetermined measurement item of a first waveform of the plurality of waveforms, as a first correction, recording the corrected first measurement point as a reference measurement point, extracting a waveform which is analogous to the first waveform, from the plurality of waveforms, and automatically correcting a measurement point for measuring the predetermined measurement item of the extracted waveform, as a second correction.

20 Claims, 4 Drawing Sheets

(51) Int. Cl.
   *A61B 5/044*      (2006.01)
   *A61B 5/0456*     (2006.01)
(58) Field of Classification Search
   USPC ......................................................... 600/516
   See application file for complete search history.

(56) References Cited

U.S. PATENT DOCUMENTS

| | | |
|---|---|---|
| 2004/0051721 A1 | 3/2004 | Ramseth |
| 2004/0054294 A1 | 3/2004 | Ramseth |
| 2004/0054295 A1 | 3/2004 | Ramseth |
| 2004/0054296 A1 | 3/2004 | Ramseth |
| 2006/0264769 A1 | 11/2006 | Satin et al. |
| 2009/0275850 A1 | 11/2009 | Mehendale et al. |
| 2011/0092838 A1 * | 4/2011 | Helfenbein .......... A61B 5/0452 600/516 |

FOREIGN PATENT DOCUMENTS

| | | |
|---|---|---|
| JP | H03-268740 A | 11/1991 |
| JP | H11-318842 A | 11/1999 |
| JP | 2004-160200 A | 6/2004 |
| JP | 2010-538728 A | 12/2010 |
| JP | 4824350 B2 | 11/2011 |
| JP | 2013-150857 A | 8/2013 |

* cited by examiner

AUTOMATIC MEASUREMENT POINT CORRECTION METHOD, AUTOMATIC MEASUREMENT POINT CORRECTION APPARATUS AND COMPUTER READABLE MEDIUM STORING AUTOMATIC MEASUREMENT POINT CORRECTION PROGRAM

CROSS REFERENCE TO RELATED APPLICATION

This application is based on Japanese Patent Applications No. 2015-146782 filed on Jul. 24, 2015, the contents of which are incorporated herein by reference.

BACKGROUND

The presently disclosed subject matter relates to a method of automatically correcting a measurement point (hereinafter, such a method is referred to as an automatic measurement point correction method), and also to an apparatus and program for automatically correcting a measurement point (hereinafter, such an apparatus is referred to as an automatic measurement point correction apparatus, and such a program is referred to as an automatic measurement point correction program), and a computer readable storage medium on which an automatic measurement point correction program is stored.

In the case where a patient is diagnosed by analyzing a vital signs information waveform having a plurality of waveforms that periodically appear on the time axis, conventionally, the diagnosis of the patient is performed based on a result of an automatic analysis which is output from an analysis apparatus for analyzing the vital signs information waveform. Alternatively, a measurement point which is determined as a point for measuring the waveforms, by the analysis apparatus is visually corrected by the operator, thereby correcting the result of the automatic analysis, and the patient is diagnosed based on the corrected result of the automatic analysis.

In the Holter electrocardiography using a Holter electrocardiogram waveform which is one kind of vital signs information waveforms, for example, there is sometimes a difference between a result of an automatic analysis which is obtained by an analysis apparatus that analyzes the Holier electrocardiogram waveform, and that of a manual analysis which is obtained by the operator through a manual analysis of the Holter electrocardiogram waveform. In the Holter electrocardiography, therefore, the operator visually corrects the measurement point which is determined by the analysis apparatus, to correct the result of the automatic analysis, and the diagnosis of the patient is then performed based on the corrected result of the automatic analysis.

Japanese Patent No. 4,824,350 discloses a technique for efficiently editing a result of an automatic analysis of a Hotter electrocardiogram waveform which is obtained by an analysis apparatus. Particularly, Japanese Patent No. 4,824, 350 discloses a technique in which the operator selects easily and intuitively characteristic heartbeat groups from a trend graph of heartbeat waveform data, whereby a result of automatic classification of the heartbeat waveform data is allowed to be edited.

In the technique disclosed in Japanese Patent No. 4,824, 350, however, many characteristic heartbeat groups exist in an enormous amount of heartbeat waveform data. In the case where a wrong measurement point is automatically determined by the analysis apparatus, the operator must visually correct the measurement point to correct the result of the automatic analysis, and therefore the correcting work takes a lot of trouble. Also in the above-described Hotter electrocardiography, furthermore, the operator must visually correct the measurement point determined by the analysis apparatus, to correct the result of the automatic analysis, and therefore the correcting work takes much trouble.

An aspect of the disclosed subject matter provides an automatic measurement point correction method in which the burden on the operator who performs a work of correcting a measurement point can be reduced.

Another aspect of the disclosed subject matter provides an automatic measurement point correction apparatus and program for realizing the automatic measurement point correction method, and a computer readable storage medium on which the automatic measurement point correction program is stored.

SUMMARY

[1] According to an aspect of the disclosed subject matter, an automatic measurement point correction method includes acquiring vital signs information waveform data indicating a vital signs information waveform having a plurality of waveforms which periodically appear on a time axis, determining a plurality of measurement points for measuring a predetermined measurement item of each waveform included in the vital signs information waveform, thereby automatically analyzing the vital signs information waveform data, causing the vital signs information waveform and measurement point displayers respectively indicating the measurement points, to be displayed on a displaying section, in accordance with an input operation by an operator, correcting a first measurement point for measuring the predetermined measurement item of a first waveform of the plurality of waveforms, as a first correction, recording the corrected first measurement point as a reference measurement point, extracting a waveform which is analogous to the first waveform, from the plurality of waveforms, and based on the reference measurement point, automatically correcting a measurement point for measuring the predetermined measurement item of the extracted waveform, as a second correction.

According to the method, the first measurement point which is corrected in accordance with an input operation by the operator is recorded as the reference measurement point. Based on the reference measurement point, the measurement point of another waveform which is analogous to the first waveform is automatically corrected.

Therefore, it is possible to provide an automatic measurement point correction method in which the burden on the operator who performs a work of correcting a measurement point can be reduced.

According to the automatic measurement point correction method, moreover, a diagnosis based on a result of an analysis of a vital signs information waveform can be quickly performed.

DETAILED DESCRIPTION OF EMBODIMENTS

Hereinafter, an embodiment of the disclosed subject matter will be described with reference to the drawings. In the description of the embodiment, description of components which are denoted by the same reference numerals as those designating components that have been already described will be omitted for the sake of convenience of description.

Figure 1:
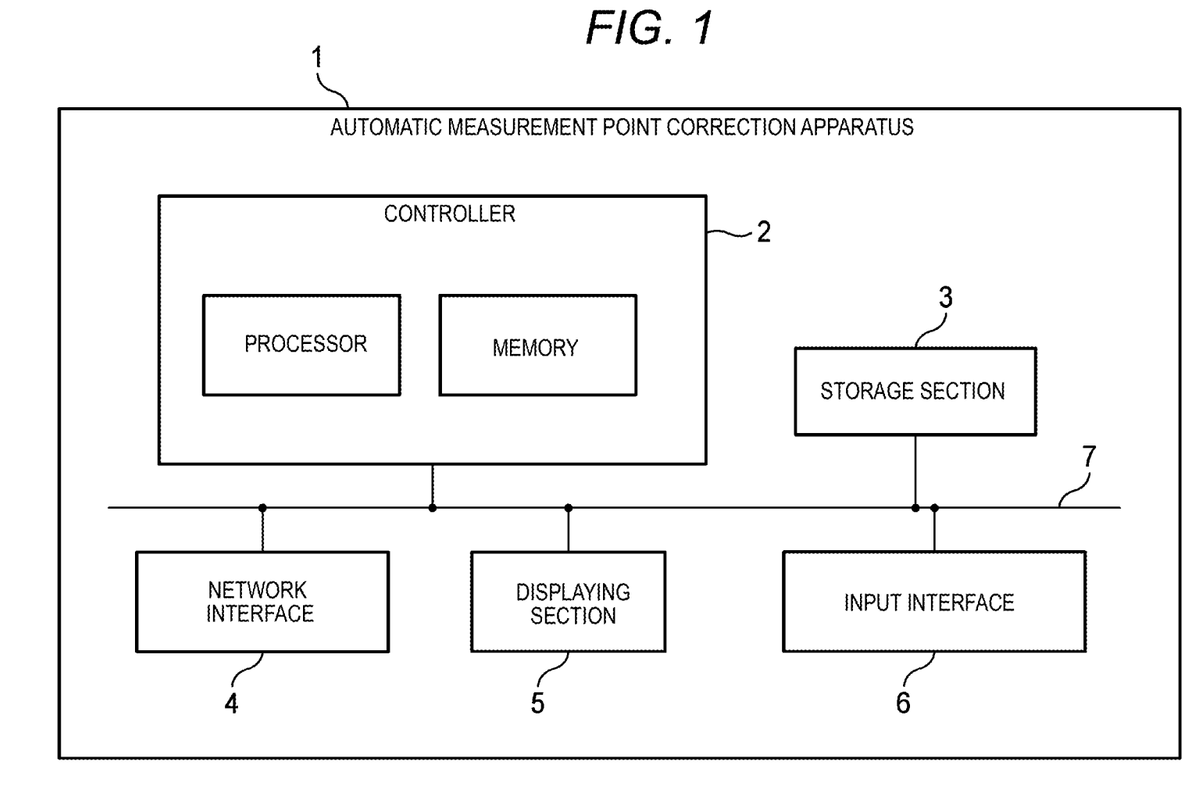
FIG. 1 is a hardware configuration diagram illustrating an automatic measurement point correction apparatus of an embodiment of the disclosed subject matter.

FIG. 1 is a hardware configuration diagram of an automatic measurement point correction apparatus 1 (hereinafter, often referred to as "correction apparatus 1" for the sake of convenience of description) of the embodiment of the disclosed subject matter. As illustrated in FIG. 1, the correction apparatus 1 may include a controller 2, a storage section 3, a network interface 4, a displaying section 5, and an input interface 6. These components are communicably connected to one another through a bus 7.

For example, the correction apparatus 1 may be a wearable device such as a personal computer, a smartphone, a tablet, or an Apple Watch, or an apparatus dedicated to the waveform analysis.

The controller 2 may include a memory and a processor. For example, the memory is configured by a ROM (Read Only Memory) in which various programs and the like are stored, a RAM (Random Access Memory) having a plurality of work area in which various programs and the like that are to be executed by the processor, and the like are to be stored. For example, the processor is a CPU (Central Processing Unit), and configured so as to develop designated programs in the various programs incorporated in the ROM or the storage section 3, in the RAM, and execute various processes in cooperation with the RAM.

Particularly, the processor may develop an automatic measurement point correction program in the RAM, and cooperate with the RAM to execute the automatic measurement point correction program, thereby enabling the controller 2 to control various operations of the correction apparatus 1. The controller 2 and the automatic measurement point correction program will be described in detail later.

The storage section 3 is a storage device such as an HDD (Hard Disk Drive), an SSD (Solid State Drive), or a flash memory, and configured so as to store programs and various data. The automatic measurement point correction program, and electrocardiogram waveform data (an example of the vital signs information waveform data) of the patient which are acquired by a Holter electrocardiogram or the like may be stored in the storage section 3.

The network interface 4 is configured so as to connect the correction apparatus 1 to a communication network such as a LAN (Local Area Network) or the Internet. For example an analysis result obtained by the correction apparatus 1 may be transmitted to a host computer placed on a LAN, through the network interface 4. Alternatively, the electrocardiogram waveform data may be wirelessly transmitted from a Holter electrocardiogram through the network interface 4.

The displaying section 5 is configured so as to display an electrocardiogram waveform (an example of the vital signs information waveform) and measurement point displaying lines which will be described later. For example, the displaying section 5 is a liquid crystal display, an organic EL display, or the like.

The input interface 6 is configured so as to receive an input operation performed by the operator who operates the correction apparatus 1, and, for example, is a touch panel which is overlaid on the displaying section 5, operation buttons which are attached to a housing, a mouse, a keyboard, or the like. While checking the electrocardiogram waveform displayed on the displaying section 5, the operator can perform a predetermined operation on the correction apparatus 1 through the input interface 6.

Figure 2:
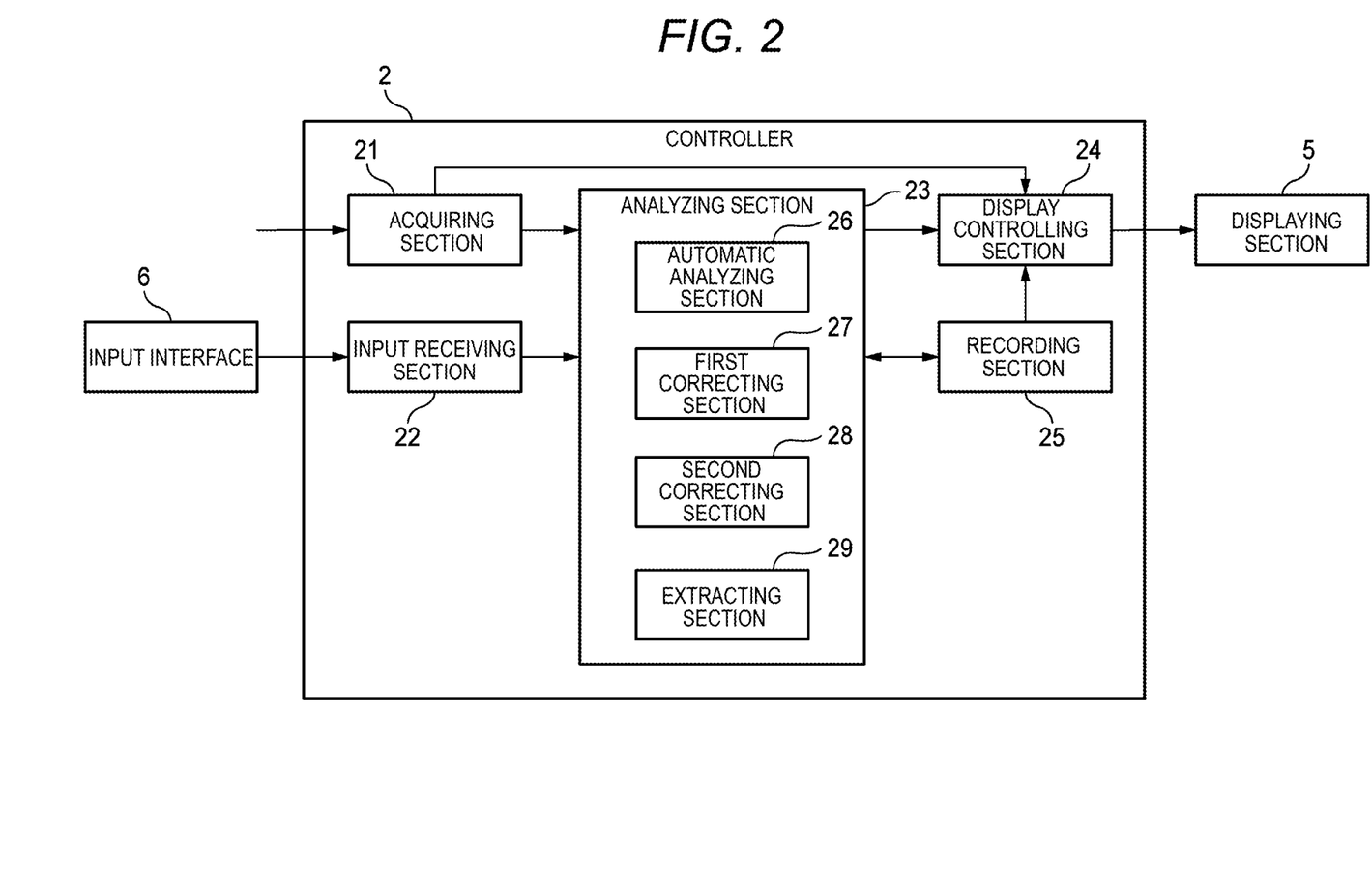
FIG. 2 is a functional block diagram of a controller.

FIG. 2 is a functional block diagram of the controller 2. As illustrated in FIG. 2, the controller 2 may include an acquiring section 21, an input receiving section 22, an analyzing section 23, a display controlling section 24, and a recording section 25.

The acquiring section 21 acquires electrocardiogram waveform data which are stored in the storage section 3, or which are received through the network interface 4. The electrocardiogram waveform data are data indicating an electrocardiogram waveform having a plurality of heartbeat waveforms that periodically appear on a time axis, and function as an example of the vital signs information waveform data.

The input receiving section 22 produces an operation signal corresponding to an input operation which is performed by the operator through the input interface 6. The analyzing section 23 analyzes the electrocardiogram waveform data, and may include an automatic analyzing section 26, a first correcting section 27, a second correcting section 28, and at extracting section 29. The automatic analyzing section 26 automatically analyzes the electrocardiogram waveform data. Particularly, the automatic analyzing section 26 determines the start points S and end points E (see FIG. 4A) of a plurality of QT intervals for measuring the QT interval of each heartbeat waveform contained in a plurality of electrocardiogram waveforms, and then calculates the QT interval. Here, the QT interval means the interval from the start of the Q wave of a heartbeat waveform to the end of the T wave. The QT interval is an example of the measurement item and the start point S and end point E of the QT interval function as an example of the measurement points. The functions of the first correcting section 27, the second correcting section 28, and the extracting section 29 will be described later.

The display controlling section 24 produces an electrocardiogram waveform based on the electrocardiogram waveform data acquired by the acquiring section 21, and causes the produced electrocardiogram waveform to be displayed on the displaying section 5. Moreover, the display controlling section 24 causes measurement point displaying lines Ls, Le (see FIG. 4A) respectively indicating the start point S and end point E of the QT interval which are acquired by the analyzing section 23, to be displayed on the displaying section 5 in a manner overlapping the electrocardiogram waveform. The measurement point displaying lines Ls, Le are examples of the measurement point displayers. The measurement point displayers are not particularly limited as far as they can display the measurement points, and may be arrows, dots, or the like in place of the lines.

The recording section 25 records an analysis result (for example, the QT interval of each heartbeat waveform, the start point S, the end point E, and a reference end point which will be described later) acquired by the analyzing section 23. The data which are recorded by the recording section 25 may be stored in the storage section 3.

Figure 3:
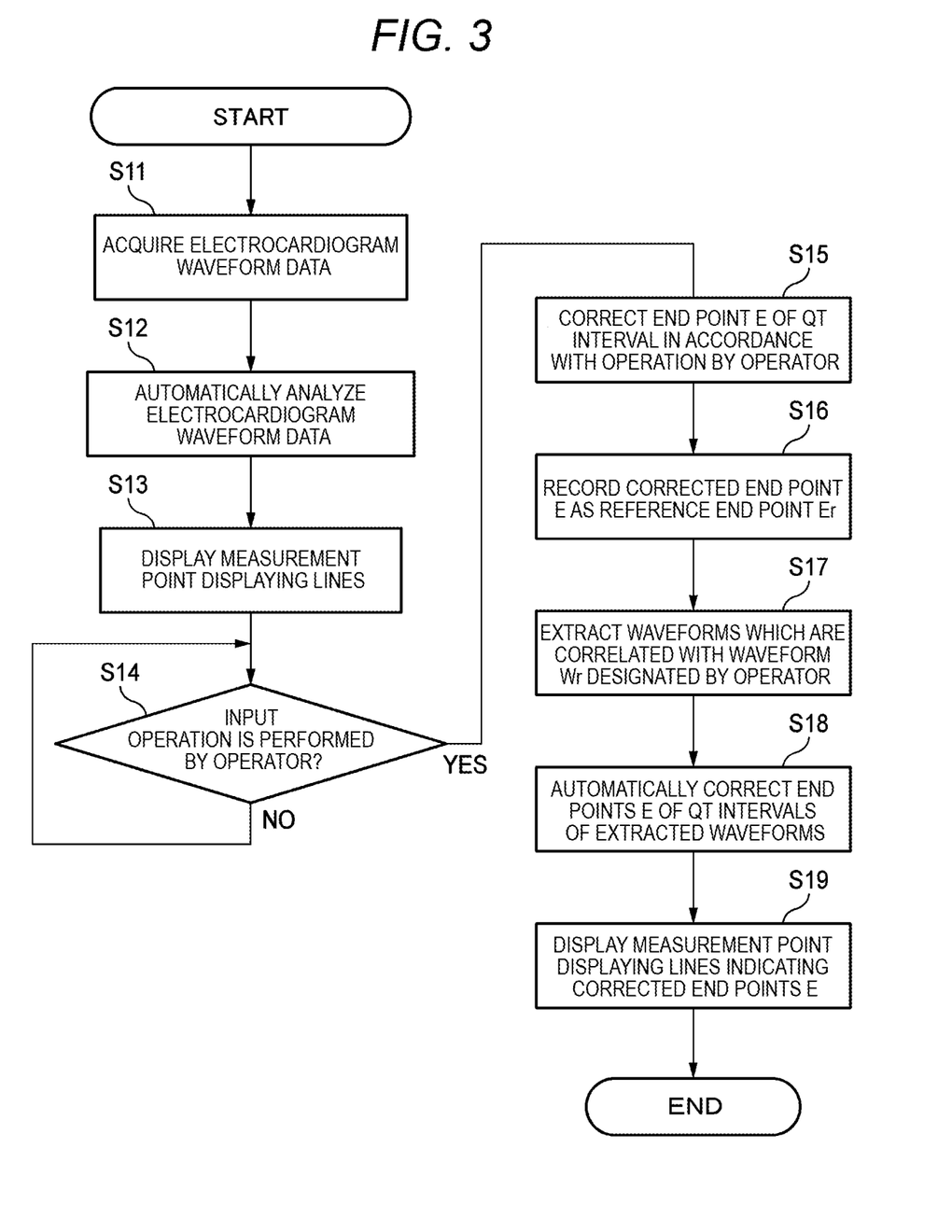
FIG. 3 is a flowchart illustrating a process of automatically correcting an end point for measuring a QT interval.
Figure 4A:
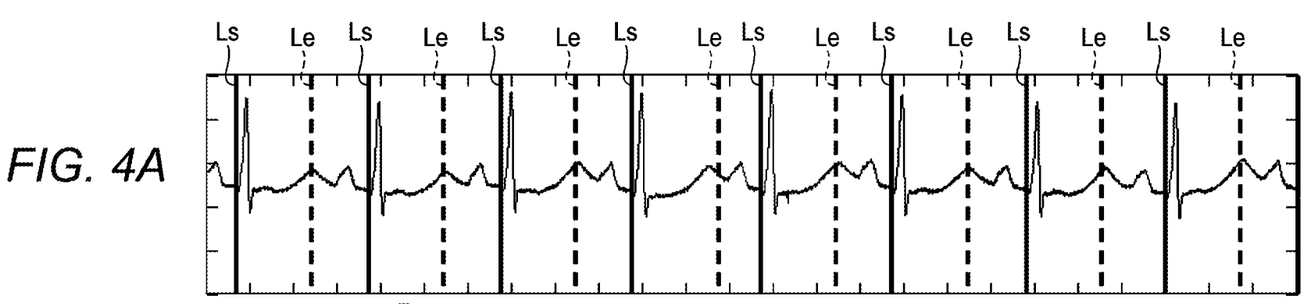
FIG. 4A illustrates an electrocardiogram waveform and measurement point displaying lines which are displayed on a displaying section before an input operation by an operator.
Figure 4B:
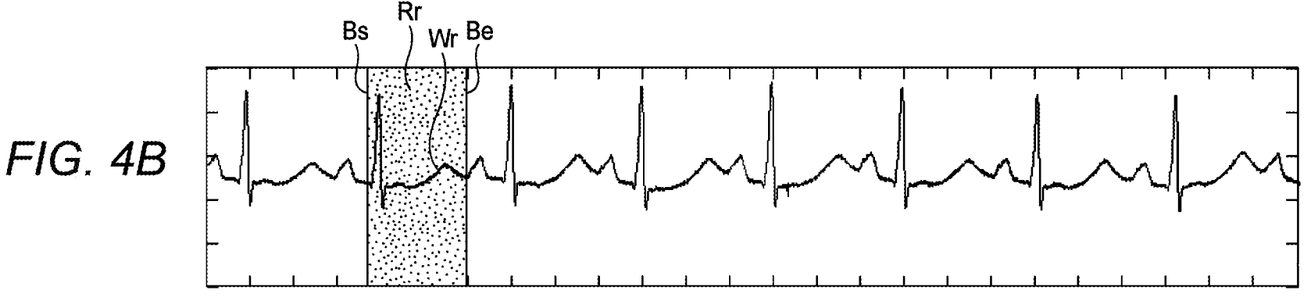
FIG. 4B illustrates the electrocardiogram waveform and reference region which are displayed on the displaying section immediately after the input operation by the operator.
Figure 4C:
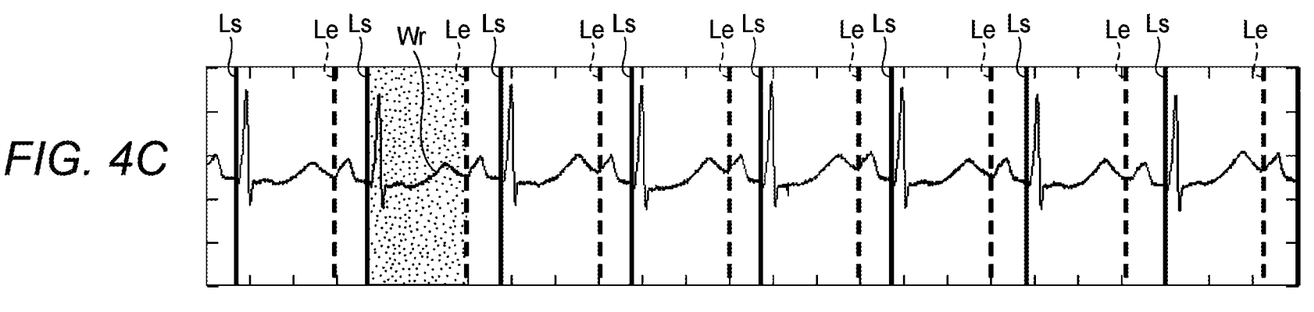
FIG. 4C illustrates the electrocardiogram waveform and measurement point displaying lines which are displayed on the displaying section after the end points of other heartbeat waveforms which are analogous to a designated heartbeat waveform are automatically corrected.

Next, a process of automatically correcting the end point E for measuring the QT interval which is an example of the measurement point will be described with reference to FIGS. 3 and 4A to 4C. FIG. 3 is a flowchart illustrating the process of automatically correcting the end point E of the QT interval. FIG. 4A illustrates an electrocardiogram waveform and measurement point displaying lines Ls, Le which are displayed on the displaying section 5 before an input operation by the operator. FIG. 4B illustrates the electrocardiogram waveform and reference region Rr which are displayed on the displaying section c immediately after the input operation by the operator. FIG. 4C illustrates the electrocardiogram waveform and measurement point displaying lines Ls, Le which are displayed on the displaying section 5 after the end points E of other heartbeat waveforms which are analogous to a heartbeat waveform Wr (first waveform) are automatically corrected. The process illustrated in FIG. 3 is performed on the assumption that the operator uses the present disclosed subject matter in order to corrects the end point E of the QT interval. In the case where the operator does not think a correction of the end point E of the QT interval is necessary (namely, in the case where the end point E which is determined by the automatic analyzing section 26 is correct), the process of measuring the QT interval is ended in step S13.

As illustrated in the flowchart of FIG. 3, the acquiring section 21 acquires in step S11 the electrocardiogram waveform data which are stored in the storage section 3, or which are received through the network interface 4. In step S12, the automatic analyzing section 26 determines the start point S and end point E for measuring the QT interval of each heartbeat waveform of the electrocardiogram waveform, thereby calculating the QT intervals of the electrocardiogram waveform data. The recording section 26 records the QT interval, start point S, and end point E of each heartbeat waveform which are analyzed by the automatic analyzing section 26.

As illustrated in FIG. 4A, next, the display controlling section 24 causes in step S13 a plurality of measurement point displaying lines Ls respectively indicating the start points S, and a plurality of measurement point displaying lines Le respectively indicating the end points E, to be displayed on the displaying section 5 while overlapping the electrocardiogram waveform.

Here, the automatic analyzing section 26 determines the start points S and the end points E by using a well-known calculation technique. However, it is difficult for the automatic analyzing section 26 to determine the correct end points E. Particularly, the automatic analyzing section 26 tends to erroneously recognize the end point E to be in the vicinity of the peak of the T wave. As illustrated in FIG. 4A, therefore, the measurement point displaying lines Le are not displayed at respective correct positions, and some measurement point displaying lines Le are displayed at positions in the vicinities of T waves, respectively. By contrast, the start points S can be determined with a relatively high accuracy by the automatic analyzing section 26. As illustrated in FIG. 4A, therefore, the measurement point displaying lines Ls are displayed at correct positions.

When an input operation is then performed on the input interface 6 by the operator (YES in step S14), the input receiving section 22 produces an operation signal corresponding to the input operation. In accordance with the operation signal produced by the input receiving section 22, thereafter, the first correcting section 27 corrects the end point E (first measurement point) for measuring the QT interval of the heartbeat waveform Wr (first waveform) (step S15). In the case where an input operation is not performed on the input interface 6 by the operator (NO in step S14), by contrast, the input receiving section 22 waits until the input operation is input.

As illustrated in FIG. 4B, when the operator sets the reference region Rr of the heartbeat waveform Wr through the input interface 6, specifically, the reference region Rr is displayed on the displaying section 5 while overlapping the electrocardiogram waveform. The left boundary line Bs of the reference region Rr indicates the start point S of the QT interval of the heartbeat waveform Wr, and the right boundary line Be indicates the end point E of the QT interval of the heartbeat waveform Wr. When the operator sets the reference region Rr with respect to the heartbeat waveform Wr so that the left boundary line Bs corresponds to the start point S, and the right boundary line Be corresponds to the end point E, namely, the input receiving section 22 produces an operation signal corresponding to the input operation by the operator. The input receiving section 22 transmits the operation signal to the first correcting section 27, and, in accordance with the operation signal, the first correcting section 27 corrects the end point E of the QT interval of the heartbeat waveform Wr which is stored in the recording section 25 (step S15). Thereafter, the recording section 25 records the end point E which is corrected by the first correcting section 27, as the reference end point Er (reference measurement point) (step S16).

Next, the extracting section 29 extracts heartbeat waveforms which are analogous to the heartbeat waveform Wr designated by the operator, from the electrocardiogram waveform (step S17). Here, the extracting section 29 extracts heartbeat waveforms which are analogous to the heartbeat waveform Wr by using a correlation function or a minimum distance method. The heartbeat waveforms which are analogous to the heartbeat waveform Wr may be determined based on a predetermined similarity. When the similarity between the heartbeat waveform Wr and another heartbeat waveform is equal to or larger than the predetermined similarity, for example, it is determined that the other heartbeat waveform is analogous to the heartbeat waveform Wr. In the case where the similarity between the heartbeat waveform Wr and another heartbeat waveform is smaller than the predetermined similarity, by contrast, it is determined that the other heartbeat waveform is not analogous to the heartbeat waveform Wr. The operator may adequately change the predetermined similarity through the input interface 6.

Next, the second correcting section 28 automatically corrects the end points E for measuring the QT intervals which are extracted by the extracting section 29, based on the reference end point Er recorded by the recording section 25 (step S18). Thereafter, the recording section 25 records the end points which are corrected by the second correcting section 28. As illustrated in FIG. 4C, the display controlling section 24 causes the measurement point displaying lines Le respectively indicating the corrected end points E, and the measurement point displaying lines Ls to be displayed on the displaying section 5 while overlapping the electrocardiogram waveform (step S19). In the embodiment, the description has been made assuming that the positions where the measurement point displaying lines Ls illustrated in FIG.

4C are displayed are identical with those where the measurement point displaying lines Ls illustrated in FIG. 4A are displayed.

According to the embodiment, the end point E which is corrected in accordance with an input operation by the operator is recorded as the reference end point Er, and the end points E of other heartbeat waveforms which are analogous to the heartbeat waveform Wr are automatically corrected based on the reference end point Er. In this regard, the QT interval is a measurement item which is hardly automatically measured, and therefore an analysis apparatus or the like tends to erroneously determine the end point E for measuring the QT interval. Therefore, the operator must manually correct all end points E which are erroneously determined, and the work of correcting end points E requires significant effort.

According to the embodiment, as described above, it is possible to provide the automatic measurement point correction apparatus 1 and automatic measurement point correction method in which the burden on the operator who performs a work of correcting the end points E can be reduced. When the automatic measurement point correction apparatus 1 or the automatic measurement point correction method is used, a diagnosis based on a result of analyzing an electrocardiogram waveform can be quickly performed, and more rapid medical service can be provided to the patient.

The automatic measurement point correction apparatus 1 and automatic measurement point correction method of the embodiment are advantageously used particularly in an electrocardiogram waveform having a large number of heartbeat waveforms.

According to the embodiment, the measurement point displaying line Le indicating the measurement point E which is corrected by the second correcting section 28 is displayed on the displaying section 5, and therefore the operator can visually check whether the corrected end point E is correct or not.

The embodiment has been described assuming that, when the reference region Rr illustrated in FIG. 4B is set, the first correcting section 27 corrects the end point E of the heartbeat waveform Wr. Various other examples of the operation by the operator may be employed. For example, it may be contemplated that the operator slides an measurement point displaying line Le (first measurement point displayer) which is displayed at an erroneous position, to the correct position through the input interface 6 such as a touch panel. In this case, the first correcting section 27 corrects the end point E of the heartbeat waveform Wr in accordance with the sliding operation which is performed on an measurement point displaying line Le by the operator, and then the second correcting section 28 automatically corrects the end points E of other heartbeat waveforms which are analogous to the heartbeat waveform Wr.

The automatic measurement point correction apparatus 1 of the embodiment may be realized in hardware or software. In order to realize the automatic measurement point correction apparatus 1 in software, for example, an automatic measurement point correction program may be pre-installed in the storage section 3 or the ROM. Alternatively, the automatic measurement point correction program may be stored on a computer readable storage medium such as a magnetic disk, an optical disk (a CD-ROM, a DVD, or the like), a magneto-optical disk (an MD or the like), an SD card, or a USB memory. In the alternative, when the storage medium is connected to the automatic measurement point correction apparatus 1, the automatic measurement point correction program which is stored in the storage medium is incorporated into the storage section 3. Then, the program incorporated in the storage section 3 is loaded into the RAM, the processor executes the loaded program, and as a result the controller 2 executes the various processes illustrated in FIG. 3. In other words, when the program is executed by the processor, the controller 2 functions as the acquiring section 21, the input receiving section 22, the analyzing section 23, the display controlling section 24, and the recording section 25.

Alternatively, the automatic measurement point correction program may be downloaded from a computer on a network such as the Internet or a LAN, through the network interface 4. Also in the alternative, similarly, the downloaded program is incorporated into the storage section 3.

Although the embodiment of the disclosed subject matter has been describe& it is a matter of course that the technical scope of the disclosed subject matter should not be limitedly interpreted by the description of the embodiment. It should be understood by those skilled in the art that the embodiment is a mere example, and may be variously changed within the scope of the disclosed subject matter as defined in the claims. The technical scope of the disclosed subject matter should be determined based on the scope of the disclosed subject matter as defined in the claims, and the scope of equivalence thereof.

Although, in the embodiment, only the QT interval is described as the measurement item, the embodiment is not limited to this. In place of the QT interval, for example, the RR interval or the like may be used as the measurement item. The RR interval means the interval between the R waves of adjacent heartbeat waveforms. In the case where the RR interval is the measurement item, the measurement point of the RR interval can be automatically corrected in accordance with a method which is substantially identical with the method of automatically correcting the end point E which is illustrated in FIGS. 3 to 4C.

Although, in the embodiment, only the automatic correction of the end point E of the QT interval is described, the embodiment is not limited to this. For example, only the start point S of the QT interval may be automatically corrected, or both the start point S and end point E of the QT interval may be automatically corrected. The method of automatically correcting the start point S is substantially identical with the method of automatically correcting the end point E which is illustrated in FIGS. 3 to 4(c). This is similarly applicable also to the RR interval and the like.

Although, in the embodiment, only electrocardiogram waveform data are described as the the vital signs information waveform data, the embodiment is not limited to this. The automatic measurement point correction apparatus and method of the embodiment may be applied to any kind of vital signs information waveform as far as the waveform has a plurality of waveforms which periodically appear on the time axis, such as pulsewaves. Namely, the automatic measurement point correction apparatus of the embodiment is particularly useful in the case where the operator must manually correct a plurality of measurement points for measuring a predetermined measurement item of a vital signs information waveform.

[1] According to an aspect of the disclosed subject matter, an automatic measurement point correction method includes acquiring vital signs information waveform data indicating a vital signs information waveform having a plurality of waveforms which periodically appear on a time axis, determining a plurality of measurement points for measuring a predetermined measurement item of each waveform included in the vital signs information waveform, thereby automatically analyzing the vital signs information waveform data, causing the vital signs information waveform and measurement point displayers respectively indicating the measurement points, to be displayed on a displaying section, in accordance with an input operation by an operator, correcting a first measurement point for measuring the predetermined measurement item of a first waveform of the plurality of waveforms, as a first correction, recording the corrected first measurement point as a reference measurement point, extracting a waveform which is analogous to the first waveform, from the plurality of waveforms, and based on the reference measurement point, automatically correcting a measurement point for measuring the predetermined measurement item of the extracted waveform, as a second correction.

[2] In the automatic measurement point correction method of [1], in the first correction, the first measurement point is corrected in accordance with a predetermined operation by the operator, the operation being performed on a first measurement point displayer indicating the first measurement point.

With the method of [2], the operator can perform the predetermined operation on the first measurement point displayer while viewing the first measurement point displayer. The first measurement point is corrected through the predetermined operation by the operator.

[3] In the automatic measurement point correction method of [1] or [2], in the extracting, a waveforms which is analogous to the first waveform is extracted from the plurality of waveforms by using a correlation function or a minimum distance method.

With the method of [3], when a correlation function or a minimum distance method is used, a waveform which is analogous to the first waveform can be extracted from the waveforms.

[4] In the automatic measurement point correction method of any one of [1] to [3] claim 1 further comprising causing a measurement point displayer indicating the measurement point which is corrected in the second correcting step, to be displayed on the displaying section.

Since the measurement point displayer indicating the measurement point which is corrected in the second correcting step is displayed on the displaying section, the operator can visually check whether the corrected measurement point is correct or not with the method of [4].

[5] In the automatic measurement point correction method of any one of [1] to [4], the vital signs information waveform is an electrocardiogram waveform having a plurality of heartbeat waveforms which periodically appear on the time axis.

The automatic measurement point correction method of [5] is advantageously used particularly in an electrocardiogram waveform having a large number of heartbeat waveforms.

[6] The automatic measurement point correction method of [5], the predetermined measurement item includes a QT interval.

The QT interval is a measurement item which is hardly automatically measured. Particularly, an analysis apparatus or the like tends to erroneously determine a measurement point for measuring the QT interval. According to the method of [6], the burden on the operator who performs a work of correcting a measurement point for measuring the QT interval can be largely reduced.

[7] In the automatic measurement point correction method of [6], the first measurement point corresponds to the end point of the QT interval, and the measurement point for the waveform which is extracted in the extracting step corresponds to the end point of the QT interval.

It is particularly difficult to, among measurement points for the QT interval, automatically determine a measurement point corresponding to the end point of the QT interval. According to the method of [7], the measurement point corresponding to the end point of the QT interval of another waveform which is analogous to the first waveform is automatically corrected based on the reference measurement point corresponding to the end point of the QT interval. Therefore, the burden on the operator who performs a work of correcting the measurement point corresponding to the end point of the QT interval can be largely reduced.

[8] According to another aspect of the disclosed subject matter, an automatic measurement point correction apparatus includes an acquiring section that acquires vital signs information waveform data indicating a vital signs information waveform having a plurality of waveforms that periodically appear on a time axis, an automatically analyzing section that determines a plurality of measurement points for measuring a predetermined measurement item of each waveform included in the vital signs information waveform, thereby automatically analyzing the vital signs information waveform data, a display controlling section that causes the vital signs information waveform and measurement point displayers respectively indicating the measurement points, to be displayed on a displaying section, a first correcting section that, in accordance with an input operation by an operator, corrects a first measurement point for measuring the predetermined measurement item of a first waveform of the plurality of waveforms, a recording section that records the corrected first measurement point as a reference measurement point, an extracting section that extracts a waveform that is analogous to the first waveform, from the plurality of waveforms, and a second correcting section that, based on the reference measurement point, automatically corrects a measurement point for measuring the predetermined measurement item of the extracted waveform.

According to the configuration of [8], the first measurement point which is corrected in accordance with an input operation by the operator is recorded as the reference measurement point. Based on the reference measurement point, the measurement point of another waveform which is analogous to the first waveform is automatically corrected. Therefore, it is possible to provide an automatic measurement point correction apparatus in which the burden on the operator who performs a work of correcting a measurement point can be reduced.

When the automatic measurement point correction apparatus is used, a diagnosis based on a result of an analysis of a vital signs information waveform can be quickly performed.

[9] According to another aspect of the disclosed subject matter, a computer readable storage medium stores an automatic measurement point correction program which causes a computer to perform an automatic correction process for correcting a measurement point. The process includes acquiring vital signs information waveform data indicating a vital signs information waveform having a plurality of waveforms which periodically appear on a time axis, determining a plurality of measurement points for measuring a predetermined measurement item of each waveform included in the vital signs information waveform, thereby automatically analyzing the vital signs information waveform data, causing the vital signs information waveform and measurement point displayers respectively indicating the measurement points, to be displayed on a displaying section, in accordance with an input operation by an operator, correcting a first measurement point for measuring the predetermined measurement item of a first waveform of the plurality of waveforms, as a first correction, recording the corrected first measurement point as a reference measurement point, extracting a waveform which is analogous to the first waveform, from the plurality of waveforms, and based on the reference measurement point, automatically correcting a measurement point for measuring the predetermined measurement item of the extracted waveform, as a second correction.

According to the configuration of [9] the first measurement point which is corrected in accordance with an input operation by the operator is recorded as the reference measurement point. Based on the reference measurement point, the measurement point of another waveform which is analogous to the first waveform is automatically corrected.

Therefore, it is possible to provide an automatic measurement point correction program in which the burden on the operator who performs a work of correcting a measurement point can be reduced.

When the automatic measurement point correction program is used, a diagnosis based on a result of an analysis of a vital signs information waveform can be quickly performed.

According to the disclosed subject matter, it is possible to provide an automatic measurement point correction method in which the burden on the operator who performs a work of correcting a measurement point can be reduced.

What is claimed is:

1. An automatic measurement point correction method comprising:
    acquiring, from one patient, vital signs information waveform data indicating a vital signs information waveform having a plurality of waveforms;
    determining a plurality of data points of the waveform data for measuring a value related to a time period of a waveform included in the vital signs information waveform, thereby automatically analyzing the vital signs information waveform data, wherein each of the determined data points corresponds to a beginning time or an end time of the time period;
    displaying the vital signs information waveform relative to a time axis on a display, the determined data points being indicated on the display relative to the vital signs information waveform;
    in accordance with an input operation by an operator, correcting a first data point corresponding to the end time of the time period of a first waveform among the determined data points, such that the end time of the time period of the first waveform is changed, as a first correction;
    recording the first data point as a reference measurement point;
    extracting a second waveform that is analogous to the first waveform from the plurality of waveforms; and
    based on the reference measurement point, automatically correcting a second data point corresponding to the end time of the time period of the second waveform such that the end time of the time period of the second waveform is changed, as a second correction.

2. The automatic measurement point correction method according to claim 1, wherein the first correction is made in accordance with a predetermined operation by the operator, the operation being performed on the display.

3. The automatic measurement point correction method according to claim 1, wherein the second waveform is extracted from the plurality of waveforms by using a correlation function or a minimum distance method.

4. The automatic measurement point correction method according to claim 1 further comprising indicating data points corrected by the second correction on the display.

5. The automatic measurement point correction method according to claim 1, wherein the vital signs information waveform is an electrocardiogram waveform having a plurality of heartbeat waveforms which periodically appear on the time axis.

6. The automatic measurement point correction method according to claim 5, wherein the value related to the waveform included in the vital signs information waveform includes a QT interval.

7. The automatic measurement point correction method according to claim 6, wherein the end time of the time period corresponds to the end point of the QT interval.

8. An automatic measurement point correction apparatus comprising:
    an acquiring section that acquires, from one patient, vital signs information waveform data indicating a vital signs information waveform having a plurality of waveforms;
    an automatically analyzing section that determines a plurality of data points of the waveform data for measuring a value related to a time period of a waveform included in the vital signs information waveform, thereby automatically analyzing the vital signs information waveform data, wherein each of the determined data points corresponds to a beginning time or an end time of the time period;
    a display controlling section that causes the vital signs information waveform to be displayed relative to a time axis on a display, the determined data points being indicated on the display relative to the vital signs information waveform;
    a first correcting section that, in accordance with an input operation by an operator, corrects a first data point corresponding to the end time of the time period of a first waveform among the determined data points, such that the end time of the time period of the first waveform is changed;
    a recording section that records the first data point as a reference measurement point;
    an extracting section that extracts a second waveform that is analogous to the first waveform from the plurality of waveforms; and
    a second correcting section that, based on the reference measurement point, automatically corrects a second data point corresponding to the end time of the time period of the second waveform such that the end time of the time period of the second waveform is changed.

9. The automatic measurement point correction apparatus according to claim 8, wherein the first correcting section corrects the determined data points in accordance with a predetermined operation by the operator, the operation being performed on the display.

10. The automatic measurement point correction apparatus according to claim 8, wherein the extracting section extracts the second waveform from the plurality of waveforms by using a correlation function or a minimum distance method.

11. The automatic measurement point correction apparatus according to claim 8, wherein the display controlling section causes an indication of the data points corrected by the second correcting section to be displayed on the display.

12. The automatic measurement point correction apparatus according to claim 8, wherein the vital signs information waveform is an electrocardiogram waveform having a plurality of heartbeat waveforms which periodically appear on the time axis.

13. The automatic measurement point correction apparatus according to claim 12, wherein the value related to the waveform included in the vital signs information waveform includes a QT interval.

14. The automatic measurement point correction apparatus according to claim 13, wherein the end time of the time period corresponds to the end point of the QT interval.

15. A computer readable storage medium storing an automatic measurement point correction program which causes a computer to perform an automatic correction process for correcting a measurement point, the process comprising:

acquiring, from one patient, vital signs information waveform data indicating a vital signs information waveform having a plurality of waveforms;

determining a plurality of data points of the waveform data for measuring a value related to a time period of a waveform included in the vital signs information waveform, thereby automatically analyzing the vital signs information waveform data, wherein each of the determined data points corresponds to a beginning time or an end time of the time period;

displaying the vital signs information waveform relative to a time axis on a display, the determined data points being indicated on the display relative to the vital signs information waveform;

in accordance with an input operation by an operator, correcting a first data point corresponding to the end time of the time period of a first waveform among the determined data points, such that the end time of the time period of the first waveform is changed, as a first correction;

recording the first data point as a reference measurement point;

extracting a second waveform that is analogous to the first waveform from the plurality of waveforms; and automatically correcting a second data point corresponding to the end time of the time period of the second waveform such that the end time of the time period of the second waveform is changed, as a second correction.

16. The computer storage medium according to claim 15, wherein the first correction is made in accordance with a predetermined operation by the operator, the operation being performed on the display.

17. The computer storage medium according to claim 15, wherein the second waveform is extracted from the plurality of waveforms by using a correlation function or a minimum distance method.

18. The computer storage medium according to claim 15 further comprising indicating data points corrected by the second correction on the display.

19. The computer storage medium according to claim 15, wherein the vital signs information waveform is an electrocardiogram waveform having a plurality of heartbeat waveforms which periodically appear on the time axis.

20. The computer storage medium according to claim 19, wherein the value related to the waveform included in the vital signs information waveform includes a QT interval.

* * * * *

UNITED STATES PATENT AND TRADEMARK OFFICE
CERTIFICATE OF CORRECTION

Page 1 of 1

PATENT NO. : 10,772,575 B2
APPLICATION NO. : 15/217096
DATED : September 15, 2020
INVENTOR(S) : Jiro Suto et al.

It is certified that error appears in the above-identified patent and that said Letters Patent is hereby corrected as shown below:

In the Specification

Column 1, Line 45, "that analyzes the Holier" should read -- that analyzes the Holter --

Column 1, Line 56, "Hotter electrocardiogram" should read -- Holter electrocardiogram --

Column 2, Line 3, "above-described Hotter" should read -- above-described Holter --

Column 4, Line 38, "28, and at extracting" should read -- 28, and an extracting --

Column 5, Line 17, "section c immediately after" should read -- section 5 immediately after --

Column 8, Line 16, "has been describe& it is" should read -- has been described, it is --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*